United States Patent [19]

Strohmeier et al.

[11] Patent Number: 4,676,653

[45] Date of Patent: Jun. 30, 1987

[54] APPARATUS FOR DETERMINING THE DIFFUSE REFLECTIVITY OF A SAMPLE SURFACE OF SMALL DIMENSIONS

[75] Inventors: Werner Strohmeier, Weilheim; Dieter Knoll, Kronberg; Erich Händler, Lampertheim-Hüttenfeld, all of Fed. Rep. of Germany

[73] Assignee: Boehringer Mannheim GmbH, Mannheim, Fed. Rep. of Germany

[21] Appl. No.: 644,870

[22] Filed: Aug. 27, 1984

[30] Foreign Application Priority Data

Mar. 2, 1984 [DE] Fed. Rep. of Germany ....... 3407754

[51] Int. Cl.[4] ............................................. G01N 21/47
[52] U.S. Cl. .................................... 356/446; 356/416
[58] Field of Search .............................. 356/445-448, 356/402, 416, 425; 250/227

[56] References Cited

U.S. PATENT DOCUMENTS

| | | | |
|---|---|---|---|
| 2,382,439 | 8/1945 | Osborn | 356/416 |
| 3,709,612 | 1/1973 | Clemens | 250/227 X |
| 4,029,419 | 6/1977 | Schumann et al. | 356/448 X |
| 4,040,747 | 8/1977 | Webster | 356/446 |
| 4,147,430 | 4/1979 | Gorgone et al. | 356/448 X |
| 4,518,259 | 5/1985 | Ward | 250/227 X |
| 4,523,853 | 6/1985 | Rosenbladt et al. | 356/448 X |
| 4,552,458 | 12/1985 | Lowne | 356/446 |

FOREIGN PATENT DOCUMENTS 0075766 4/1983 European Pat. Off. .
0075767 4/1983 European Pat. Off. .

*Primary Examiner*—R. A. Rosenberger
*Attorney, Agent, or Firm*—Felfe & Lynch

[57] ABSTRACT

The present invention relates to an apparatus for determining the diffuse reflectivity of a sample surface of small dimensions, especially of the test field of a test strip for determining the substances contained in a body fluid. The apparatus has a semiconductor light emitter, especially a light-emitting diode, for the emission of visible or infrared light to the sample surface, a measuring receiver for receiving the light diffusely reflected by the sample surface and producing an electrical signal corresponding thereto, an evaluating means including an electronic circuit for converting the receiver signal to a value corresponding to the diffuse reflectivity, and a reference channel using the light from the same emitter for the calibration of the apparatus and for the elimination of errors of measurement caused by variations of the emitter or of other electronic components.

15 Claims, 4 Drawing Figures

APPARATUS FOR DETERMINING THE DIFFUSE REFLECTIVITY OF A SAMPLE SURFACE OF SMALL DIMENSIONS

BACKGROUND OF THE INVENTION

The present invention relates to an apparatus for determining the diffuse reflectivity of a sample surface of small dimensions, especially the test field of a test strip for determining the substances contained in a body fluid, the apparatus having a semiconductor light emitter, preferably a light-emitting diode (LED), for the transmission of visible or infrared light to the sample surface, a measuring receiver for receiving the diffusely reflected light from the sample surface and for the production of an electrical signal corresponding thereto, evaluating means including electronic circuit means for converting the received signal to a value corresponding to the diffuse reflectivity, and a reference channel using the light of the same emitter for the calibration of the apparatus and for the elimination of errors of measurement which are caused by changes in the emitter or other electronic components. As used hereinafter and in the claims, the term "light" includes visible and infrared light.

Apparatus for determining the diffuse reflectivity of a surface are known in many different forms. However, apparatus which are intended to serve for determining the reflectivity of the test field of a test strip must satisfy very special requirements. It is precisely for apparatus of this kind, however, that there is an increasing need, because it has been possible for several years to manufacture test strips with such accuracy that the color change that takes place on them can be used, if precisely evaluated by the apparatus, for the quantitative determination of substances contained in body fluids, especially blood. Particularly important in this connection is the determination of blood sugar by means of test strips and corresponding evaluating apparatus whereby it has become possible for diabetics themselves to determine their blood sugar levels at relatively brief intervals. Consequently it has become possible to establish dosages of medicaments, especially insulin, more precisely than before, and consequently to reduce considerably the occurrence of the feared late consequences of diabetes.

Apparatus suitable for this purpose must satisfy very high accuracy requirements. On the other hand, they must achieve this accuracy under marginal conditions such as were not commonly encountered in the prior-art apparatus for determining reflectivity. In particular, only a very small area is available for measurement. For example, a test strip to be measured preferentially with the apparatus of the present invention has two directly adjoining test fields with a total surface measuring 6×6 mm, which is divided in the middle. Of the resultant test field width of 3 mm, only a width of about 1.2 mm is available for evaluation by reflection photometry.

In order to be made available to large numbers of users, the apparatus must be economical to produce. Other important requirements are compactness and battery operation. Considerable progress in this regard has been achieved by an apparatus which uses a semiconductor light emitter, especially a light-emitting diode (LED) whose light is used for the diffuse illumination of the sample surface through an Ulbricht sphere. The light diffusely reflected by the sample surface is detected by a light receiver through a special diaphragm design. Further details are described in the European patent application under Publication No. 75,766. With this apparatus, using a light-emitting diode as the light source, a precision can surprisingly be achieved such as formerly could be achieved only by using light sources of high constancy and intensity. It is particularly advantageous that the apparatus is in the form of a two-channel apparatus having a measuring channel and a reference channel. The term "reference channel." as used herein and in the claims, means an optical ray path which differs from the optical ray path of the measuring channel at least to the extent that it does not include the sample surface. Reference channels are known in a variety of forms in the photometric art. The reference channel of the above-mentioned apparatus is so designed that it is possible, after a single calibration procedure performed in the manufacture of the apparatus, to determine the diffuse reflectivity of the test fields of test strips without further calibration measurements.

Despite these very good results, the apparatus referred to above is not satisfactory in every respect. In particular, the Ulbricht sphere involves considerable manufacturing expense. Also, the amount of space which it requires is not available under all circumstances, especially when a plurality of closely adjacent test fields are to be evaluated on a so-called multiple-field test strip, without the need for moving them successively into the range of a single measuring apparatus. This would require several measuring instruments disposed closely side by side, which can be achieved only with very great difficulty if illumination through an Ulbricht sphere is used.

It is therefore an object of the present invention to make available an apparatus for determining the diffuse reflectivity of a sample surface which, while using a semiconductor light emitter as the source of radiation, will permit very precise measurement, plus compact construction and low cost of manufacture.

SUMMARY OF THE INVENTION

This object is achieved in an apparatus of the kind specified above by equipping the reference channel in such a manner that the central ray of the beam used for the reference measurement coincides upon leaving the emitter with that of the beam used for the illumination of the specimen, so that the same orientation of the light leaving the semiconductor light emitter is used for the sample measurement and for the reference measurement.

The invention utilizes the knowledge that semiconductor light emitters, especially light-emitting diodes (LED's) (hereinafter only light-emitting diodes will be mentioned for the sake of simplicity, but without limitation of the general meaning), have a light distribution curve which varies in a complex manner with changes in current and temperature, and not simply in the sense of an affine representation. In other words, as temperature and current change, the ratio of the light intensity of two particular alignments changes. Wherever LED's have been used heretofore in conjunction with the reflective photometric evaluation of test strips, with the provision of a reference channel, these differences have been disregarded, resulting in correspondingly poor accuracy in the apparatus. In the apparatus mentioned above, using an Ulbricht sphere, a very high accuracy results in spite of the above-described changes in the light distribution curve of the light-emitting diodes because the Ulbricht sphere integrates the light emitted by the light-emitting diode through all solid angles and the light thus integrated is used not only for illuminating the sample surface but also a reference surface situated in the reference channel.

The present invention teaches the use of the same alignment of the light-emitting diode which is used for the sample measurement also for the reference measurement, thereby bringing it about that the above-mentioned changes of the light distribution curve with current and temperature affect the measuring channel and the reference channel in the same manner. By obtaining the quotient, it is thus possible to eliminate errors over long periods of time without the need for complex components which require a considerable amount of space.

The reference channel performs its function of detecting as accurately as possible both long-term and short-term fluctuations of the beam of light used for the specimen illumination in view of the special characteristic of the light-emitting diode all the better, the more thoroughly the beam used for the reference measurement ("reference beam") coincides with the beam used for illuminating the sample ("sample beam"). This is optimally the case when not only the central ray of both beams coincides, but also both beams have the same contour. It has been found experimentally, however, that sufficient accuracy can be achieved if the apparatus is so designed that a number of geometrical conditions are satisfied which are the subject matter of preferred embodiments of the present invention. Of particular importance is the magnitude of the solid angle that is covered in each case by the two beams. This solid angle preferably is relatively small in order to permit a small angle between the detection axis and the illumination axis, without problems with the mirror reflection produced by the sample surface ("gloss problem"). At the same time, this will facilitate the closely adjacent arrangement of several measuring channels for several closely adjacent test fields of a multiple-field test strip. On the other hand, the solid angles in both beams should be largely identical in order to detect as precisely as possible the changes in the light beam used for sample illumination. For this purpose the solid angle of the light emitted by the light-emitting diode, which is used both for sample illumination and for the reference channel, preferably should be less than 0.1 steradian, more preferably less than 0.01 steradian. The two solid angles preferably should not differ from one another by more than a factor of 10, more preferably not more than a factor of 2, it being important for the solid angle of the beam of the reference ray to be completely within that of the measuring ray, i.e., the reference beam preferably is a section of the sample beam.

As stated above, the invention is especially suitable for apparatus which measure small sample surfaces and themselves have small dimensions. Preferably, therefore, the distance between the light emitting diode and the sample surface should amount to no more than 200 mm, more preferably not more than 50 mm. In this connection it is to be stressed that an optical system can not be reduced in size simply by linearly reducing the dimensions of a previously known larger optical system. Instead, specific problems arise in this case, which have to do with the fact, for example, that the components, such as especially light sources and receivers, cannot be arbitrarily changed in scale. The invention takes into consideration the special requirements of a small system using light emitting diodes as light sources.

Preferably, the distance between the semiconductor emitter and the sample surface amounts to at least 5 mm, and very preferably at least 10 mm. If the distance is shorter, it becomes difficult on the one hand to achieve the preferred small solid angles by means of correspondingly small apertures. Also, the smaller this distance is, the greater is the effect of errors in the positioning of the sample surface with regard to its distance from the light emitting diode.

The invention can be embodied in many different ways. For example, a reference receiver can be disposed in back of the sample surface in line with the light beam illuminating it. This receiver detects the light emitted by the LED as long as no sample surface is in the beam path. Then the sample is inserted and the diffusely reflected light is measured by a measuring receiver separate from the reference receiver. Disadvantages of this system are relatively complex manipulation, and the fact that the sample measurement and the reference measurement cannot be performed simultaneously, so that such a design does not permit the elimination of brief fluctuations in the LED.

These disadvantages can be avoided by inserting a component in the beam path between the LED and the sample surface to deflect the reference beam. A suitable component is, for example, a moving mirror, which can be fastened to a chopper. If the frequency of movement is sufficiently high, even extremely brief fluctuations in the intensity will be detected. Especially preferred, however, is the use of a beam splitter which constantly splits off a certain portion of the light beam used for sample illumination and feeds it to the reference channel.

The use of a beam splitter is common in the optical art. In the European patent application under Publication No. 81,947 a beam splitter is used in conjunction with a table-top instrument which is intended primarily for the determination of the phosphorescent luminescence of a sample surface. The beam splitter in this instrument serves to divide the luminous flux emitted by a 1000-volt, 7.5-Joule xenon arc lamp, and to direct it on the one hand against the sample, and on the other hand onto a comparator surface. The two rays are alternately fed through a moving mirror chopper to a common measuring receiver. This is useful in the previously known design for eliminating the considerable, brief fluctuations in the intensity of the high-voltage flash lamp. The previously known design has a complex construction involving a number of optical systems which are necessary, for example, for focusing the light beam in the vicinity of the chopper and thus to achieve a sufficiently steep flank angle. Although special problems involved in the measurement of phosphorescent luminescence are solved by this prior art within the framework of a comparatively complex and expensive table-top instrument, this published patent application gives no suggestion that a beam splitter can also be used for the reference beam of a hand instrument operating with battery-powered light-emitting diodes.

To keep the cost of construction low, it is preferred, in the apparatus of the invention, to use a separate reference receiver for the reference channel. This eliminates the use of components which otherwise would be necessary in order to feed both beams alternately to a common receiver. The two receivers are preferably of identical construction and connected to a corresponding evaluating electronic circuit, such as the one described, for example, in the European patent application under Publication No. 75,767.

In order to make the reference channel as completely equal to the measuring channel as possible, it might appear desirable to dispose also in the reference channel, in back of the beam splitter if desired, a surface that diffusely reflects the light. If desired, a different condensing component (diffuser) might also be suitable, such as a scattering glass. Surprisingly, however, it has been found that a reference beam path having no such component at all is capable not only of detecting brief fluctuations of the intensity of the light from the LED, but also of being used, after only a single factory calibration, as a standard for the measurement of diffuse reflectivity. The elimination of this component improves the long-term stability of the instrument and avoids the loss of intensity necessarily involved in a diffuser.

The beam splitter, by its division ratio, essentially determines the intensity of the light arriving at the reference receiver. Now, if this division ratio is made such, in accordance with a preferred embodiment, that the electrical signal produced by the reference receiver is, for example, just as great as that produced by the measuring receiver, if a sample surface of very high diffuse reflectivity of virtually 100% is being measured, it is possible to assure that the signal produced by the measuring receiver is always smaller in practice than that produced by the reference receiver. In this manner the evaluation to be performed in the electronic evaluating circuit can be simplified.

Optimum accuracy, on the other hand, can be achieved by means of an alternative preferred embodiment, in which the division ratio of the beam splitter is made such that the signal of the reference receiver will be about identical with that of the measuring receiver when a sample having diffuse reflectivity of about 10% is inserted. Since this value is the logarithmic mean of the overall range of 0 to 100%, an optimum equalization of the signals to be processed by the measuring channel and the reference channel will be achieved with this preferred embodiment in the average case, and hence an improvement in accuracy of measurement.

The beam splitter can be in various forms, such as beam splitter cubes or prisms. Especially preferred, however, is the use of a plate of transparent material, especially glass or plastic, having plane-parallel surfaces and disposed between the semiconductor emitter and the sample such that the beam passing through the plate is fed to the sample and the beam reflected by the emitter side of the plate is fed to the reference channel receiver. Such an embodiment is simple and inexpensive. The division ratio thus achieved has proven useful in practice. A simple means for additionally affecting the division ratio is the insertion of a second similar plate in the beam path of the reference channel; in this case only the reflected beam is fed to the reference receiver, but the beam passing through the plate is largely absorbed.

As previously stated, the invention is addressed particularly to an apparatus which, with a single calibration performed at the factory, i.e., without repeated measurement of a reflection standard, will, through its entire life, permit the determination of the reflectivity of different sample surfaces. To this end, it is especially preferred that the geometry of the beam paths in the measuring channel and in the reference channel be kept constant throughout the life of the instrument. In practice, this means especially that the sample surface is to be so precisely positioned with respect to its surface perpendiculars that the required accuracy of measurement is not impaired by variations in the distance from the light emitters and measuring receivers. In addition, all of the components determining the beam paths preferably are fixedly mounted. If components are used which, by their reflectivity or transmission, affect the intensity of the light arriving in the measuring receiver and reference receiver, care must be taken that they do not vary to a degree impairing the accuracy of measurement. Here, again, the advantage of simple design using as few component parts as possible is evident.

The invention can be used to special advantage for the measurement of two closely adjacent sample surfaces, especially for the simultaneous determination of the reflectivity of the two test fields of a so-called dual field test strip. Especially good results are achieved in this case if completely separate measurement channels are used for the measurement of both test fields, each channel also having its own reference channel. This is true even when the light for the illumination of the sample surface is derived from a common LED.

In accordance with the invention, apparatus for determining the diffuse reflectivity of a sample surface of small dimensions comprises a semiconductor light emitter for the emission of light for a light beam having a central ray to the sample surface. The apparatus includes a measuring receiver for receiving the light diffusely reflected from the sample surface and for producing an electrical signal corresponding thereto. The apparatus also includes evaluating means coupled to the receiver including electronic circuit means for converting the receiver signal to a measurement corresponding to the diffuse reflectivity. The apparatus also includes a reference channel coupled to the evaluating means and using the light of the same emitter for a light beam having a central ray for the calibration of the apparatus and for substantially minimizing at least measurement errors caused by variations in the emitter. The reference channel is so constructed that the central ray of the beam used for the reference measurement coincides, upon leaving the emitter, with the central ray of the beam used for the sample illumination, so that the same allignment of the light leaving the semiconductor light emitter is used for the sample measurement and the reference measurement.

For a better understanding of the present invention, together with other and further objects thereof, reference is made to the following description, taken in connection with the accompanying drawings, and its scope will be pointed out in the appended claims.

BRIEF DESCRIPTION OF THE DRAWINGS

The invention will be further explained hereinbelow in conjunction with an embodiment represented in the drawings, wherein.

DESCRIPTION OF THE PREFERRED EMBODIMENT

Figure 1:
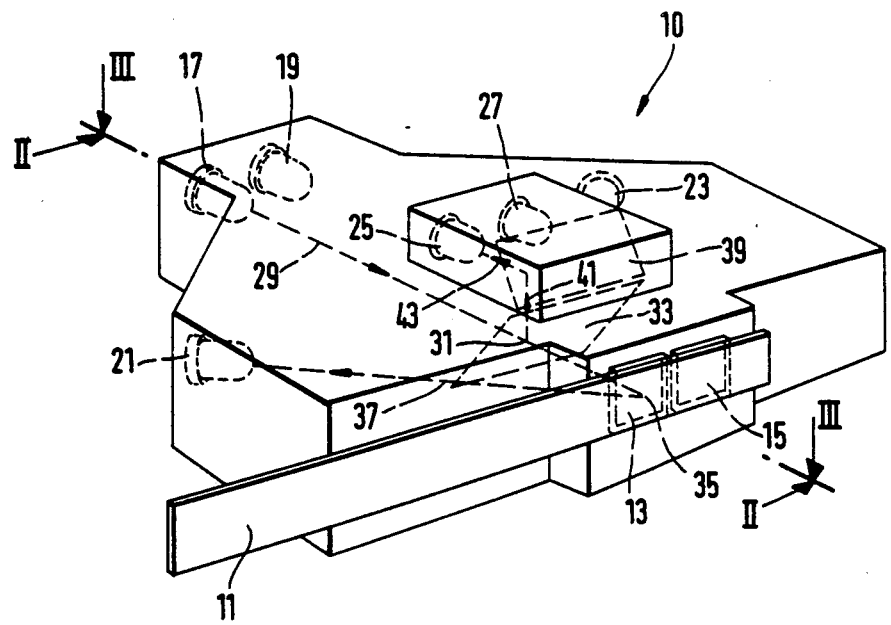
FIG. 1 is a perspective, diagrammatic representation of the optical unit of an apparatus of the invention.

FIG. 1 is a diagrammatic, highly simplified perspective representation of an optical unit 10 of a preferred embodiment of the instrument of the invention. The test strip 11 can be seen, which is a dual-field test strip, whose test fields 13 and 15 are to be evaluated. FIG. 1 serves primarily for illustrating the course taken by the rays in the optical unit. Details are to be seen in FIGS. 2 to 4.

The optical unit represented preferably has two completely separate measuring systems for the two test fields 13 and 15 and therefore has two LED's 17 and 19, two measuring receivers 21 and 23, and two reference receivers 25 and 27. For the sake of simplicity, only one of the ray paths is represented in broken lines with arrows.

The central ray of the beam emitted from the LED 17, insofar as it is simultaneously the central ray of the test beam and of the reference beam when it leaves the LED, is identified as 29. At the dividing point 31 it passes through the beam splitter 33 and strikes the test field approximately at the center 35. The second part of the central ray of the test beam, which is no longer common with the reference beam, is identified as 30. The light beam diffusely reflected by the test field 13 to the measuring receiver 21 is identified as 37. The light path from the LED 17 to the measuring receiver 21 constitutes the measuring channel.

At the dividing point 31, a portion of the beam used for illumination of the sample is reflected upwardly by the beam splitter 33 against the second beam splitter 39. The central ray of this portion of the beam used for the reference measure is designated by the number 41. The beam again reflected by beam splitter 39, whose central ray is indicated at 43, falls upon the reference receiver 25.

Figure 2:
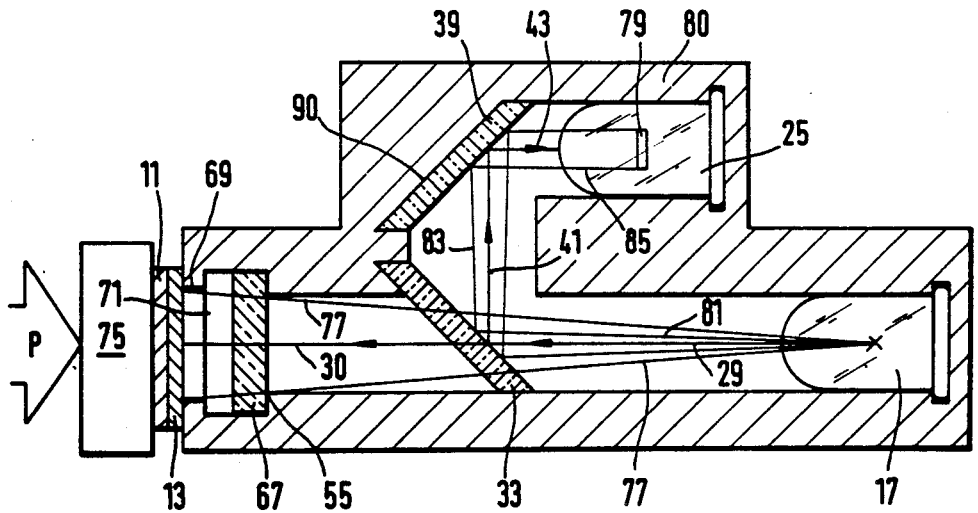
FIG. 2 is a longitudinal section through an optical unit as in FIG. 1, the plane of section being indicated by line II—II in FIG. 1.
Figure 3:
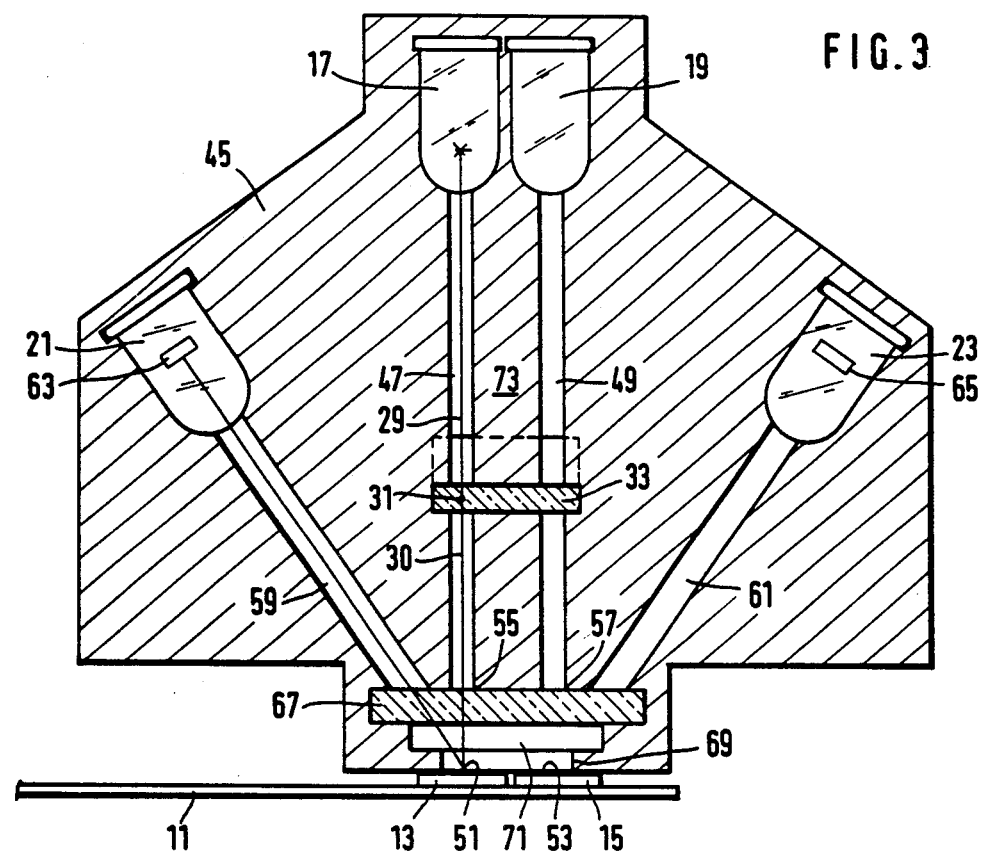
FIG. 3 is a longitudinal section through an optical unit as in FIG. 1, the plane of section being indicated at III—III in FIG. 1.
Figure 4:
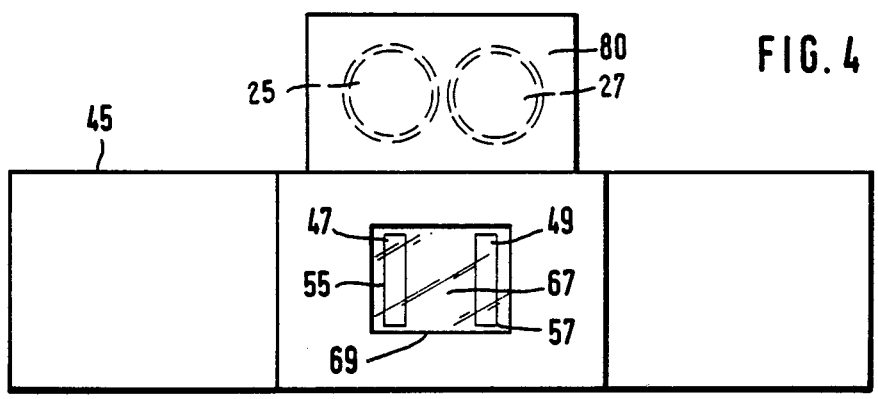
FIG. 4 is a view of the optical unit of FIG. 1 as seen from in front of the measurement aperture.

FIGS. 2 to 4 show further details of the design, also in diagrammatic form. FIG. 2 is a cross section in the plane defined by the central ray of the beam 29, 41 and 43 used for the reference measurement. This plane runs perpendicular to the surface of the test strip 11 which is in the measuring position, intersecting the test field perpendicular to the length of the latter. FIG. 3 is a section through the plane in which the central ray of the beam 30 used for sample illumination and the central ray ("axis of detection") of the light 37 diffusely reflected by the sample surface to the measuring receiver 21 is located. This plane likewise runs approximately through the center of the test field being measured and perpendicularly to the surface of the test strip that is in the measuring position, but it extends in its longitudinal direction and therefore is perpendicular to the plane described previously.

In FIG. 3 there can be seen, in a housing block 45, two light shafts 47 and 49 through which the light emitted by the LED's 17 and 19 falls perpendicularly on the sample surfaces of the test fields 13 and 15 of the test strip 11. The beam used in both measuring channels for sample illumination passes through the first beam splitter 33, which is seen only in cross section in FIG. 3. The beam splitter in the embodiment represented preferably is a glass or plastic plate common to both measuring channels. The reasons for this are technical reasons relating to production. The two parallel light shafts 47 and 49, as it can be seen in FIG. 3, are separated optically by the partition 73, so that component 33 optically forms separate beam splitters for each of the two measuring channels associated with the test fields 13 and 15. Up to the dividing point 31, the central ray of the beam 30 used for sample illumination is identical to that of the beam used for the reference measurement. Both are provided in this part with the reference number 29. The beam used for sample illumination is defined at the test-strip ends 55 and 57 of the light shafts 47 and 49 by the width of the latter. These therefore form the aperture mask of the beam used for sample illumination. It can be seen that only a narrow section of the light leaving each of the LED's is used for sample illumination.

The light diffusely reflected by the sample surfaces 51 and 53 passes through light shafts 59 and 61, respectively, to the measuring receivers 21 and 23. It can be seen that the light shafts 59 and 61 are wider than light shafts 47 and 49. This brings it about that all of the light diffusely reflected by the illuminated portion of the test fields 13 and 15, i.e., by the sample surfaces 51 and 53, toward the photosensitive surfaces 63 and 65 of the measuring receivers 21 and 23 is detected. If the light shafts 59 and 61 were made too narrow, there would be the danger that they might mask off a portion of the light to be detected by the measuring receivers 21 and 23. The result of this might be that, in the event of a slight change in the positioning of the test strip with respect to the LED's 17 and 19, a variation of the signal might occur.

At the test-strip end of the light shafts 47, 49, 59 and 61 is an optical window 67. It can be seen that the optical window 67 is set back from the measuring aperture 69 and leaves a recess 71. In this manner, the optical window 67, which is provided for the avoidance of contamination of the components of the optical unit 10, cannot be contaminated by the measuring fields 13 and 15 which of course are wetted with the sample fluid, especially blood.

Locating the optical window 67 directly at the ends 55 and 57 of the light shafts 47 and 49 assures that no light reflected at the optical window 67 will reach the measuring receivers 21 and 23.

The partition 73 separating the two light shafts 47 and 49 terminates at the optical window 67. In the recess 71 between the optical window 67 and measuring aperture 69, no separation is provided between the two measuring channels for test fields 13 and 15. In order nevertheless to reliably prevent any influence of one by the other, only the LED's and measuring receivers of one measuring channel are operated at one time by the electronic control system. Although this electronic separation of the two measuring channels is preferred, one skilled in the art can easily resort to a system in which an optical separation of the two measuring channels is achieved also in recess 71 by suitable masking.

All components, especially the LED's, the photosensors and the beam splitter or splitters, preferably are precisely fitted into corresponding recesses in the housing block 45, so that their position will not change as the apparatus is used even over long periods of time, and thus the geometry of the beam paths will be preserved.

Thus it is possible reliably to determine for long periods of time the diffuse reflectivity of sample surfaces after only a single calibration performed in the manufacture of the apparatus, if it is assured that the sample surface is situated at the same distance from the LED's 17 and 19 with a precision suitable for the desired accuracy of measurement. For this reason the test fields 13 and 15 are pressed against the measuring aperture 69 by a pressure device 75 represented diagrammatically in FIG. 2, which assures that the contact pressure, symbolized in FIG. 2 by the arrow P, remains constant with sufficient accuracy under all conditions of measurement. A device of this kind is described in the European patent application having the Publication No. 37,484.

In FIG. 2 can be seen the section 29 perpendicular to the length of the test strip 11, of the beam that is used for sample illumination in the one measuring channel and passes through the first beam splitter 33 and the optical window, falling on the sample surface 51 at the measuring aperture 69. The fringe rays are indicated at 77. It can be seen that the beam used for sample illumination is substantially wider in the plane of Fig.2 than it is in the plane of FIG. 3. Its rectangular shape can be seen especially well in FIG. 4, in which the test-strip ends 55 and 57 of light shafts 47 and 49 are represented, which define the beam used for sample illumination.

The solid angle corresponding to this beam can be computed in a known manner from the area of the rectangle illuminating the test field 13 and the distance of the test field from the light source. The rectangular shape of the light shaft was selected in order to adapt the beam used for sample illumination to the shape of the useful area of test fields 13 and 15. It can also be seen from the figs. that the test surfaces 51 and 53 illuminated by the LED's 17 and 19 amount to only a relatively small portion of the surface areas of test fields 13 and 15. This is done because the marginal areas of the test fields can be less uniform and can therefore be less suitable for the evaluation. As a result, however, of the entire test field surface of, for example, 3×6 mm, only a portion of about 1.5×4 mm is available for the evaluation.

As can also be seen in FIG. 2, the reference receiver 25 is situated in a compartment 80 on the housing block 45. The beam used for the reference measurement, whose fringe rays are identified by the reference numbers 81, 83 and 85, passes through the two beam splitter plates 33 and 39 to the reference receiver 25.

The solid angle of the light emitted by the LED 17 and used by the reference beam is determined by the size of the photosensitive surfaces 79 of the reference receiver 25. It is shown enlarged in the figure for the sake of clarity. In a photodiode used preferentially as the reference receiver, the photosensitive surface measures only about 1 mm×1 mm. It can clearly be seen in FIG. 2 that the solid angle of the reference beam lies wholly within the solid angle of the sample beam. This is true not only in the plane of FIG. 2, but also in the plane of FIG. 3 in which the corresponding fringe beams, however, have not been represented.

Beam splitters are preferred which, as represented in FIG. 2, use plane-parallel plates of a transparent material such as glass or plastic. At the first beam splitter 33, if glass is used, approximately 4 to 5% of the incident light is reflected vertically upward by the beam splitter disposed at an angle of 45°. The second beam splitter, in the embodiment represented, is used virtually as a mirror serving for additional beam attenuation. This is because practical experiments have shown that the above-mentioned preferred division ratio can easily be achieved if a second beam splitter is used, the two deflections of the beam having the additional advantage that it results in an especially compact assembly. The light passing through the second beam splitter 39 is substantially absorbed on its back by the largely absorbent adjacent surface 90. The degree of beam attenuation that can be achieved by the second beam splitter can advantageously be controlled by making surface 90 more or less absorbent.

To illustrate the dimensions involved, some data on a preferred embodiment of the instrument of the invention are given herewith:
Light shaft 47,
    length: 11 mm
    cross section: 0.8 mm×3.2 mm
Light shaft 59,
    length: 10.5 mm
    cross section: 1.0 mm×3.2 mm
Distance of test strip from the LED's: 20.5 mm
Angle of measurement=angle between the central rays 30 and 37: 35°.
Thickness of beam splitter plate: 0.8 mm.

While there has been described what is at present considered to be the preferred embodiment of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. Apparatus for determining the diffuse reflectivity of a test field of small dimensions of a test carrier for determining substances contained in a body fluid, comprising:
    a semiconductor light emitter for the emission of light for a light beam having a central ray to the test field;
    a measuring receiver for receiving the light diffusely reflected from the test field and for producing an electrical signal corresponding thereto;
    evaluating means coupled to said receiver including electronic circuit means for converting the receiver signal to a measurement value corresponding to the diffuse reflectivity; and
    a reference channel coupled to said evaluating means and using the light of the same emitter for a light beam having a central ray for the calibration of the apparatus and for substantially minimizing at least measurement errors caused by variations in the emitter, the reference channel being so constructed that the central ray of the beam used for the reference measurement coincides, upon leaving the emitter, with the central ray of the beam used for the test field illumination, the solid angles of both beams being smaller than 0.1 steradian, and said solid angles of both beams differing by a factor of not more than 10, so that the same alignment of the light leaving the semiconductor light emitter is used for the test field measurement and the reference measurement.

2. Apparatus in accordance with claim 1, in which the solid angles of both beams are smaller than 0.01 steradian.

3. Apparatus in accordance with claim 1, in which the solid angle used by said beam used for the reference channel is situated entirely within the solid angle used by said beam used for the test field illumination.

4. Apparatus in accordance with claim 1, in which said two solid angles differ by not more than a factor of two.

5. Apparatus in accordance with claim 1, in which the distance between said semiconductor light emitter and the test field is between 2 and 200 mm.

6. Apparatus in accordance with claim 5 in which the distance between said semiconductor light emitter and the test field is between 10 and 50 mm.

7. Apparatus in accordance with claim 1, in which said reference channel includes a beam splitter which is disposed in the light path between said semiconductor light emitter and the test field, and deflects a portion of the light beam aimed at the test field for said reference channel.

8. Apparatus in accordance with claim 7, in which said reference channel includes a reference receiver separate from the measuring receiver for the light reflected by the sample.

9. Apparatus in accordance with claim 8, in which the beam splitter has such a division ratio that the electrical signal produced by the reference receiver is approximately as great as that produced by the measuring receiver when a test field of high diffuse reflectivity is measured.

10. Apparatus in accordance with claim 8, in which said beam splitter has such a division ratio that the electrical signal produced by said reference receiver is approximately as large as that produced by the measuring receiver if a test field of a diffuse reflectivity of about 10% is measured.

11. Apparatus in accordance with claim 7, in which said beam splitter comprises a plate of transparent material having plane-parallel surfaces, which is disposed between said semiconductor light emitter and the test field, the ray penetrating said plate being guided to the test field and the ray reflected by the emitter side of the plate being guided to said reference receiver.

12. Apparatus in accordance with claim 1, in which said measuring receiver is in a measuring channel and in which the geometry of the ray paths of said measuring channel and of said reference channel is held constant over the life of the apparatus.

13. Apparatus in accordance with claim 12, in which the test field is positioned so precisely in the direction of the surface normals that the required accuracy of measurement is not impaired by changes in the distance between the test field and said semiconductor light emitter and said measuring receiver, respectively.

14. Apparatus in accordance with claim 1, in which, for measuring two test field situated closely together, two beams derived from one or more semiconductor emitters are provided for the separate illumination of the test field and two separate reference channels associated therewith are provided.

15. Apparatus in accordance with claim 14 in which said two beams derived from one or more semiconductor emitters are derived from different semiconductor emitters.

* * * * *

UNITED STATES PATENT AND TRADEMARK OFFICE
CERTIFICATE OF CORRECTION

PATENT NO. : 4,676,653

DATED : June 30, 1987

INVENTOR(S) : Werner Strohmeier, et al.

It is certified that error appears in the above-identified patent and that said Letters Patent is hereby corrected as shown below:

Column 10, line 68 for "2 and 200" read -- 5 and 200 --.

Column 12, line 18 for "field" read -- fields --.

Column 12, line 21 for "field" read -- fields --.

Signed and Sealed this

Fourth Day of July, 1989

Attest:

DONALD J. QUIGG

*Attesting Officer*     *Commissioner of Patents and Trademarks*